United States Patent
Lenich et al.

(10) Patent No.: US 10,631,989 B2
(45) Date of Patent: Apr. 28, 2020

(54) SURFACE REPLACEMENT IMPLANT FOR THE DISTAL HUMERUS

(71) Applicant: OT MEDIZINTECHNIK GmbH, Munich (DE)

(72) Inventors: Andreas Lenich, Planegg (DE); Ulrich Schreiber, Munich (DE)

(73) Assignee: OT MEDIZINTECHNIK GMBH, München (DE)

( * ) Notice: Subject to any disclaimer, the term of this patent is extended or adjusted under 35 U.S.C. 154(b) by 79 days.

(21) Appl. No.: 15/561,430

(22) PCT Filed: Mar. 23, 2016

(86) PCT No.: PCT/EP2016/056450
§ 371 (c)(1),
(2) Date: Sep. 25, 2017

(87) PCT Pub. No.: WO2016/151047
PCT Pub. Date: Sep. 29, 2016

(65) Prior Publication Data

US 2018/0116807 A1 May 3, 2018
US 2018/0344467 A9 Dec. 6, 2018

(30) Foreign Application Priority Data

Mar. 24, 2015 (DE) .......... 10 2015 104 442
Mar. 25, 2015 (DE) .......... 10 2015 104 480

(51) Int. Cl.
*A61F 2/38* (2006.01)
*A61F 2/30* (2006.01)
(Continued)

(52) U.S. Cl.
CPC ........ *A61F 2/3804* (2013.01); *A61F 2/30749* (2013.01); *A61F 2/30771* (2013.01); *A61B 17/16* (2013.01); *A61B 17/8897* (2013.01); *A61B 2017/1602* (2013.01); *A61F 2/30942* (2013.01); *A61F 2002/3009* (2013.01);
(Continued)

(58) Field of Classification Search
CPC ............ A61F 2/3804; A61F 2002/3822; A61F 2002/3827
See application file for complete search history.

(56) References Cited

U.S. PATENT DOCUMENTS 3,798,679 A * 3/1974 Ewald .................. A61F 2/38
623/20.31
4,242,758 A * 1/1981 Amis ................ A61B 17/1604
606/87
(Continued)

FOREIGN PATENT DOCUMENTS

DE 2823406 A1 12/1978
EP 98466 A1 1/1984
WO 2011/035145 A1 3/2011

*Primary Examiner* — Brian A Dukert
(74) *Attorney, Agent, or Firm* — Millman IP Inc.

(57) ABSTRACT

The present invention relates to a partial joint replacement (1000), encompassing a shell-like segment (100) with a concave inner contour (3) for the arrangement on at the bone structure of a patient, wherein the segment (100) comprises a lateral section (5) and a medial section (7) along a longitudinal direction (x), and wherein the outer contour (1) of the segment (100) comprise in longitudinal direction (x) at least one inflection point (9).

20 Claims, 13 Drawing Sheets

(51) Int. Cl.
*A61B 17/16* (2006.01)
*A61B 17/88* (2006.01)

(52) U.S. Cl.
CPC ............ *A61F 2002/30062* (2013.01); *A61F 2002/30092* (2013.01); *A61F 2002/3093* (2013.01); *A61F 2002/30224* (2013.01); *A61F 2002/30578* (2013.01); *A61F 2002/30784* (2013.01); *A61F 2002/30841* (2013.01); *A61F 2002/30845* (2013.01); *A61F 2002/30878* (2013.01); *A61F 2002/30884* (2013.01); *A61F 2002/3809* (2013.01); *A61F 2002/3822* (2013.01); *A61F 2002/3827* (2013.01); *A61F 2310/00029* (2013.01); *A61F 2310/00179* (2013.01)

(56) References Cited

U.S. PATENT DOCUMENTS

| | | | |
|---|---|---|---|
| 4,378,607 A | | 4/1983 | Wadsworth |
| 5,030,237 A | * | 7/1991 | Sorbie ................... A61B 17/15 623/20.11 |
| 2011/0266265 A1 | * | 11/2011 | Lang ................... A61F 2/30756 219/121.72 |

\* cited by examiner

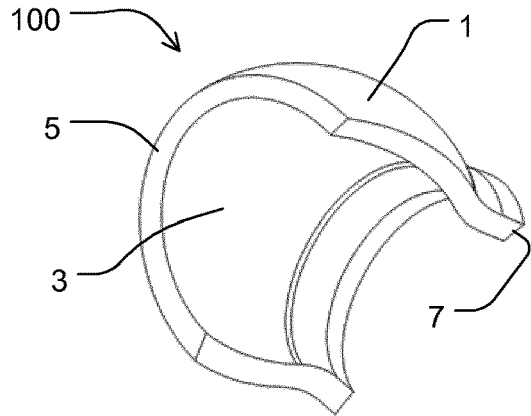
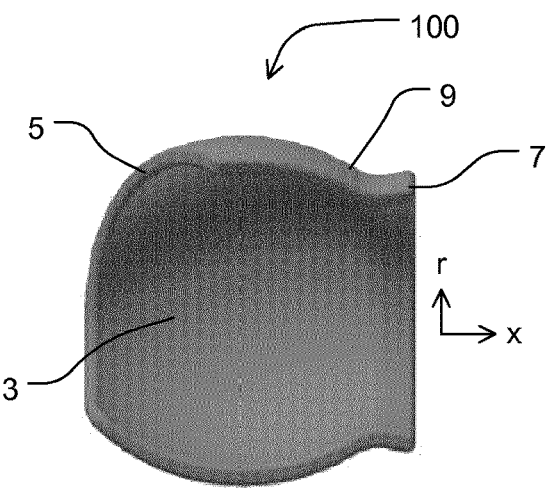
Fig. 1a  Fig. 1b
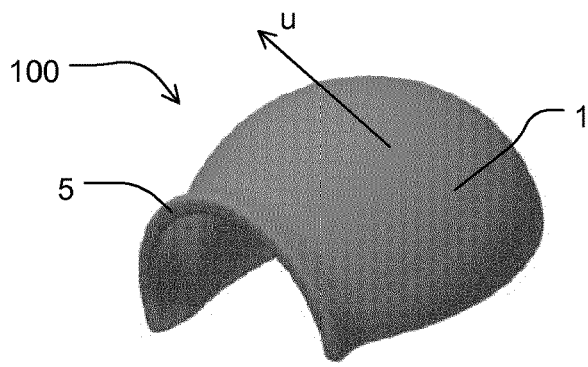
Fig. 1c
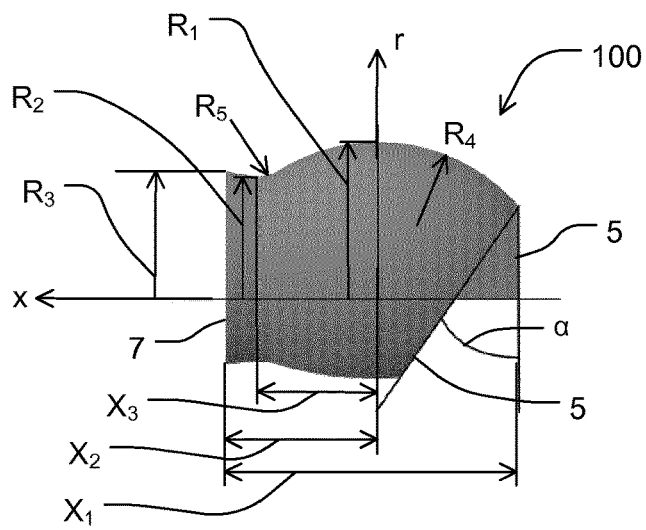
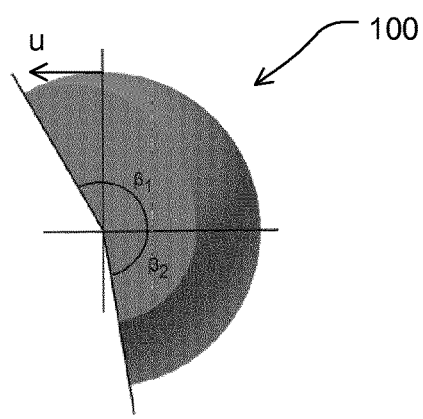
Fig. 1d  Fig. 1e

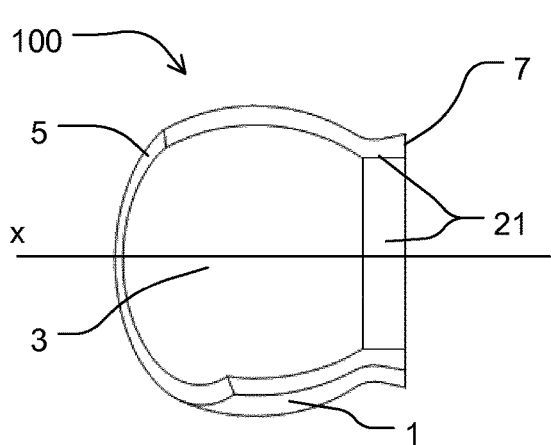
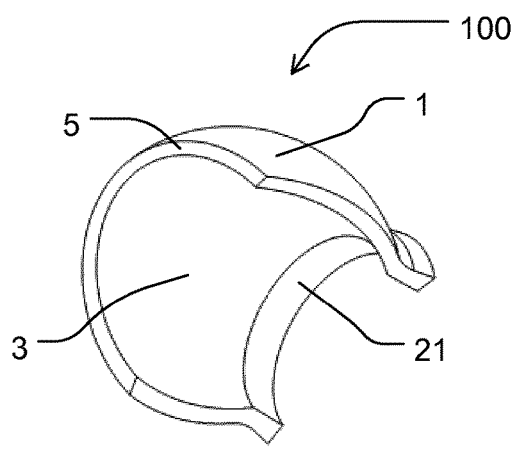
Fig. 4a        Fig. 4b
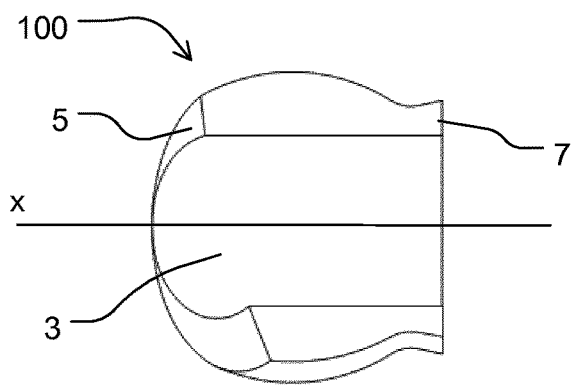
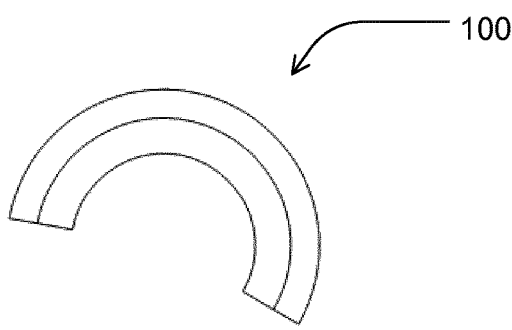
Fig. 5a        Fig. 5b
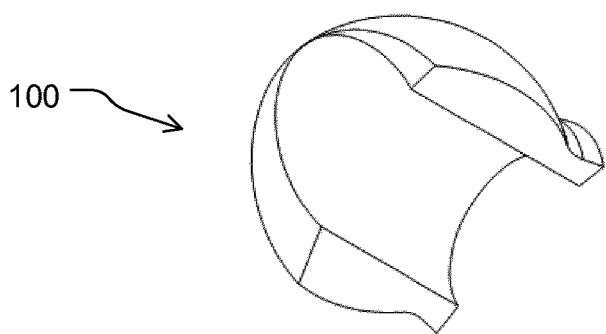
Fig. 5c

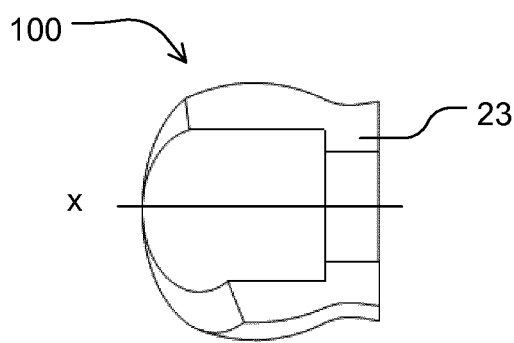
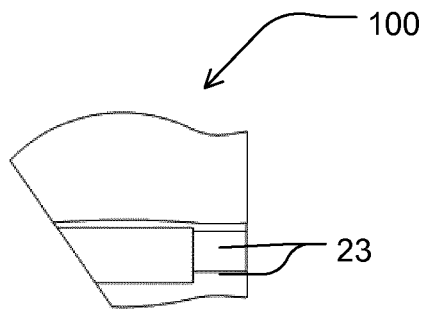
Fig. 6a   Fig. 6b
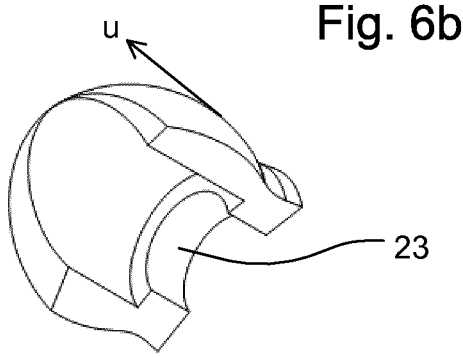
Fig. 6c
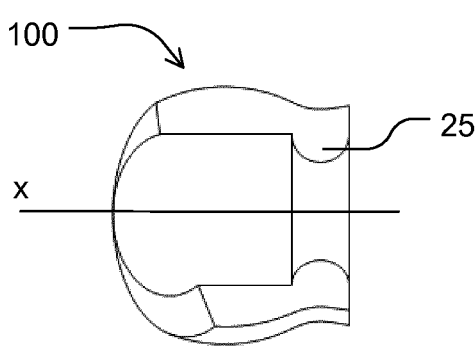
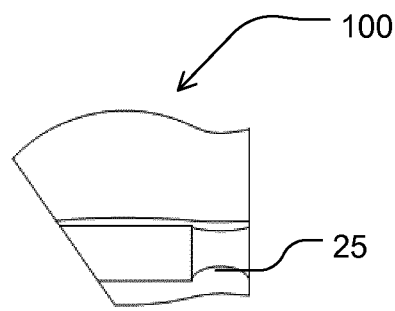
Fig. 7a   Fig. 7b
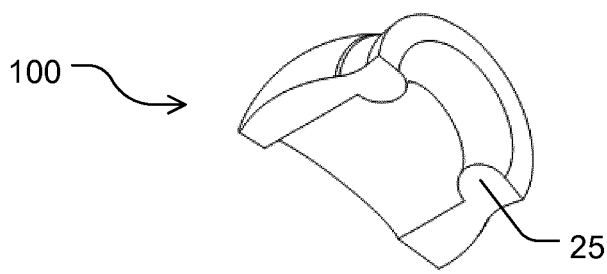
Fig. 7c

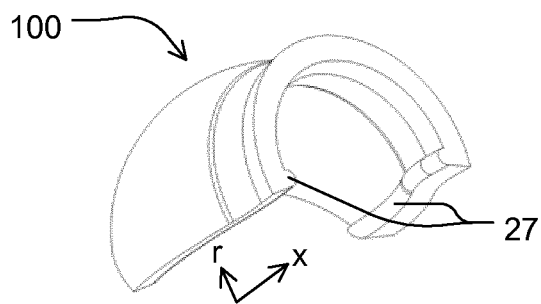
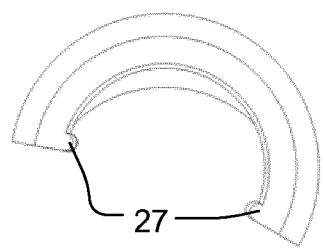
Fig. 8a　　　　　　Fig. 8b
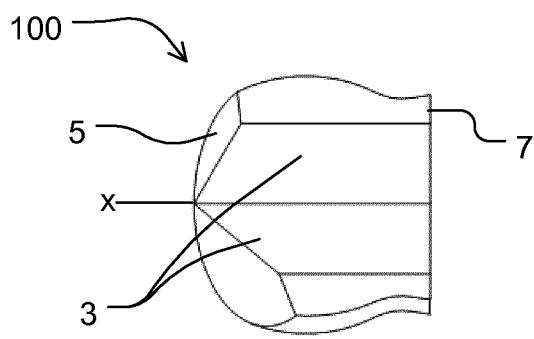
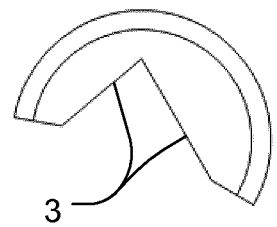
Fig. 9a　　　　　　Fig. 9b
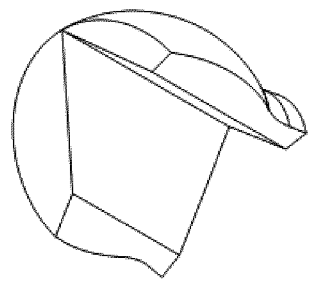
Fig. 9c
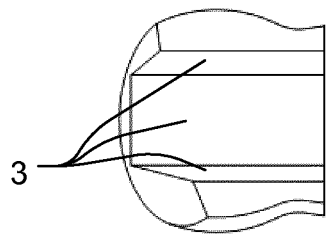
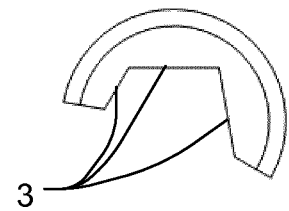
Fig. 10a　　　　　　Fig. 10b

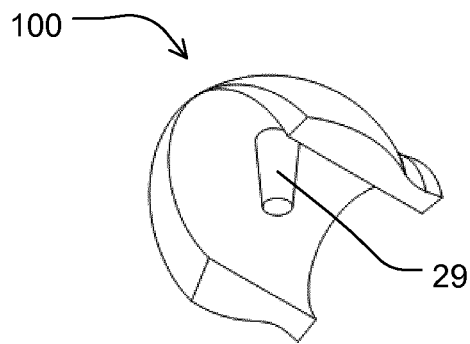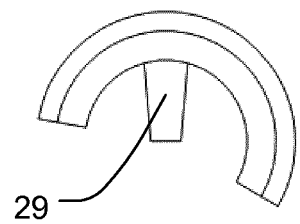
Fig. 11a Fig. 11b
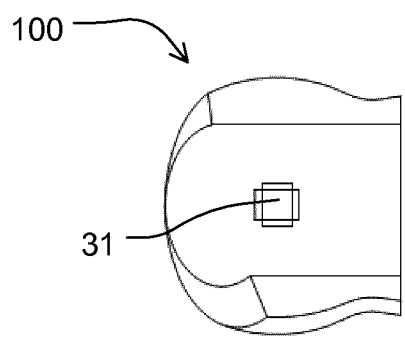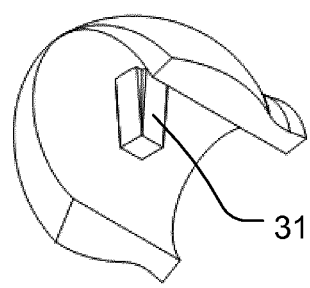
Fig. 12a Fig. 12b
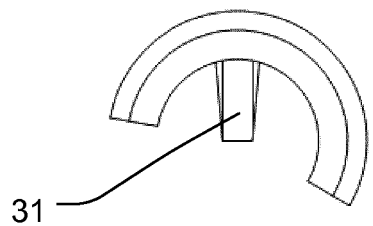
Fig. 12c

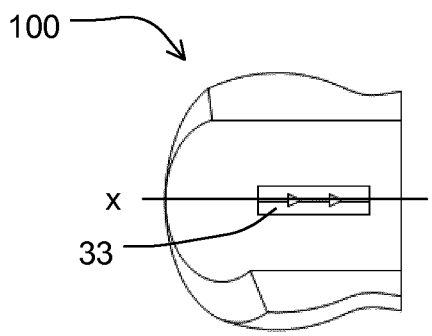
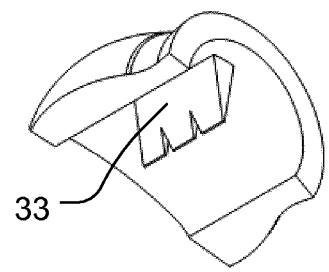
Fig. 13a          Fig. 13b
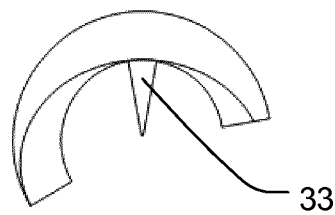
Fig. 13c
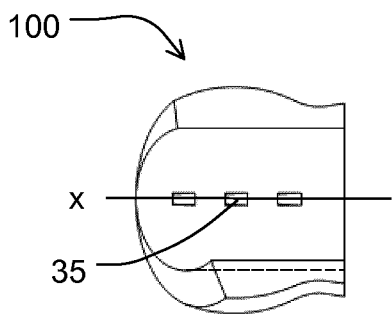
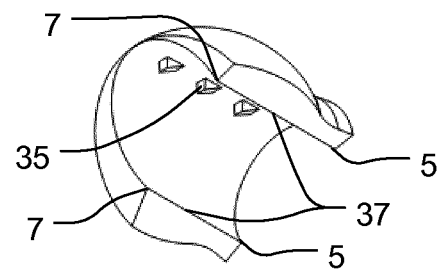
Fig. 14a          Fig. 14b
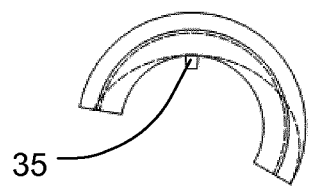
Fig. 14c

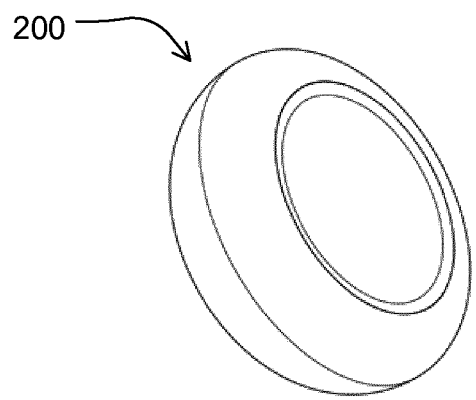
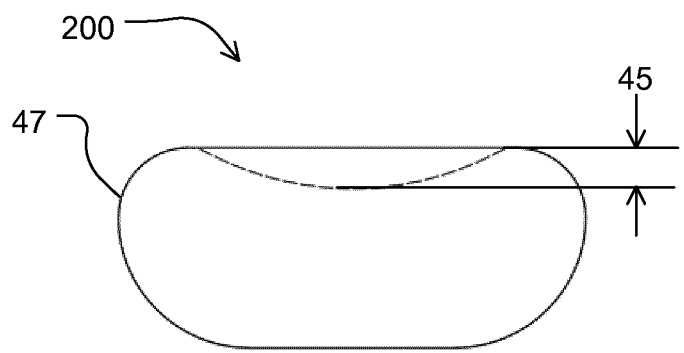
Fig. 17a Fig. 17b
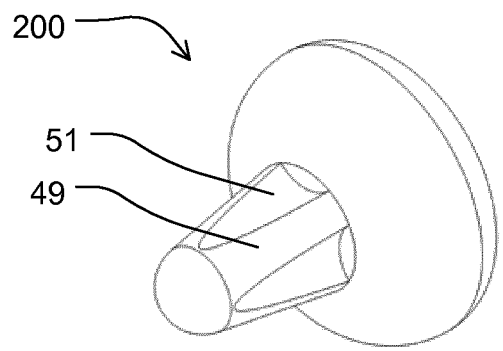
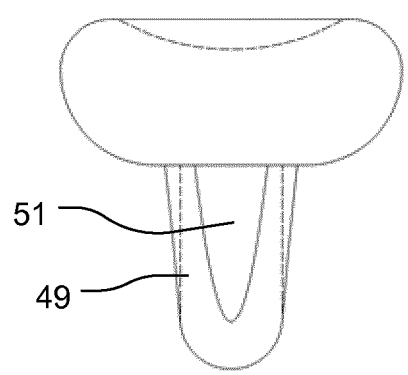
Fig. 18a Fig. 18b

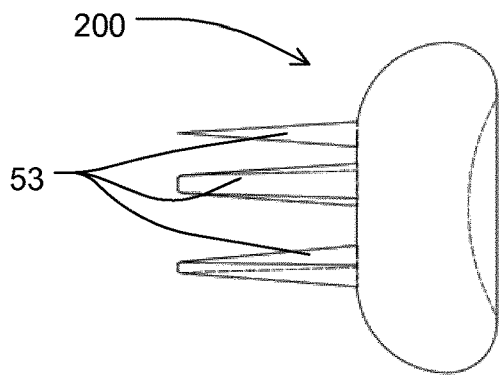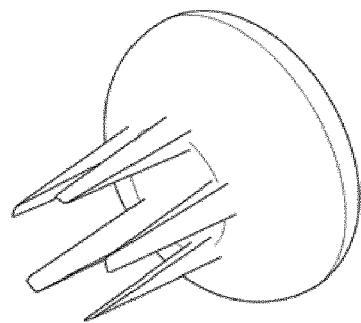
Fig. 19a  Fig. 19b
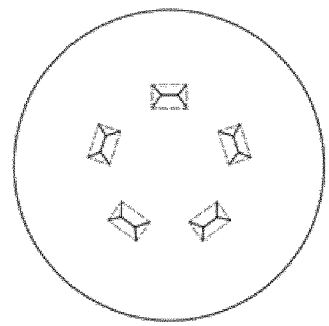
Fig. 19c
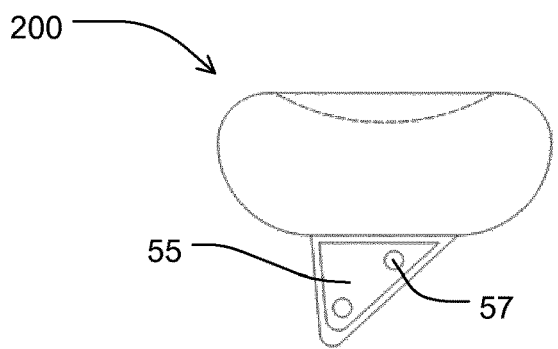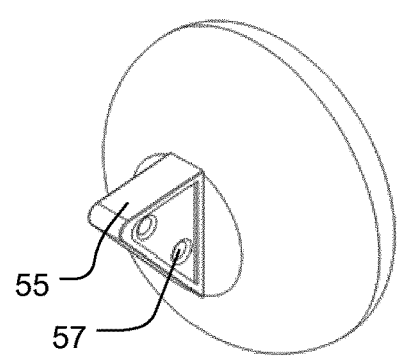
Fig. 20a  Fig. 20b
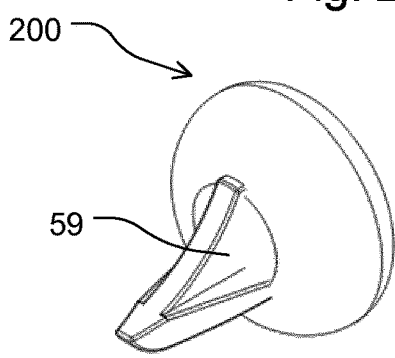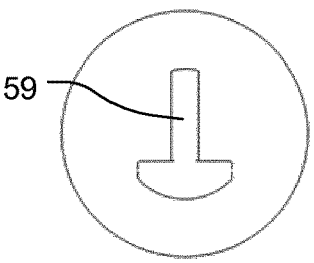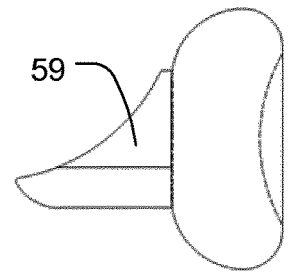
Fig. 21a  Fig. 21b  Fig. 21c

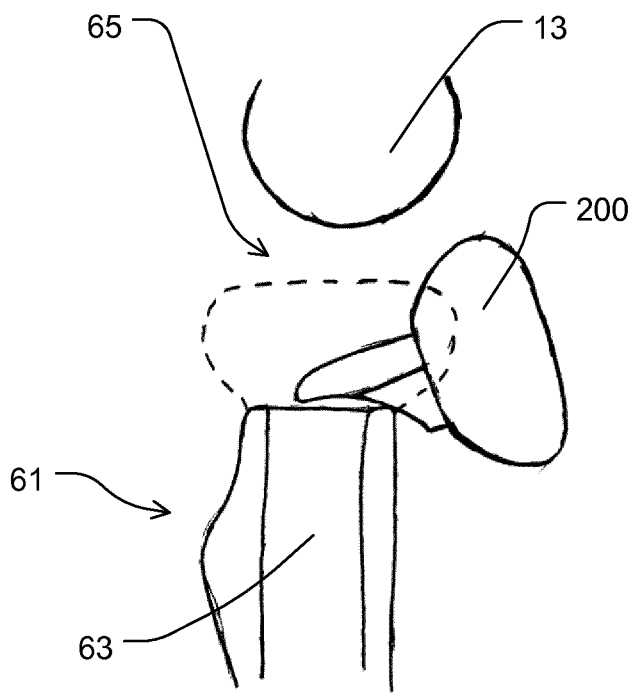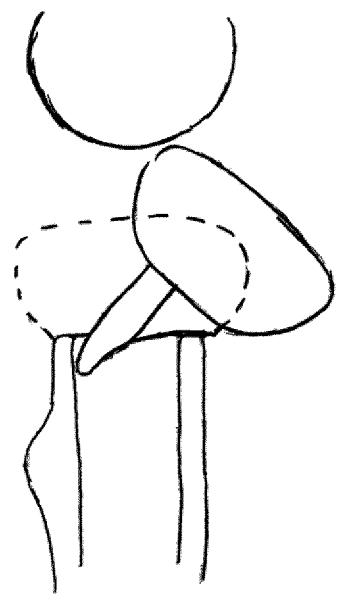
Fig. 22a  Fig. 22b
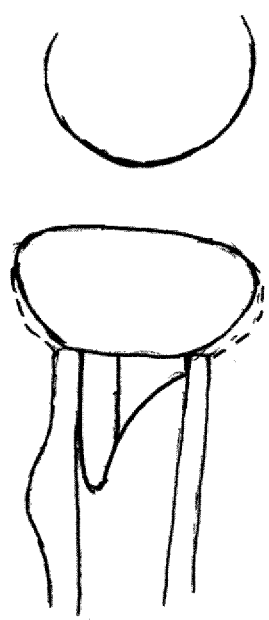
Fig. 22c

SURFACE REPLACEMENT IMPLANT FOR THE DISTAL HUMERUS

The present invention relates to a medical apparatus or to a medical surface replacement implant according to claim 1, in particular designed as an elbow joint replacement, partial elbow joint replacement, elbow joint implant, total joint replacement or total elbow joint replacement. The present invention further relates to a set according to claim 25 and a method according to claim 26.

Joints are subject to wear, which can affect the cartilage of the joint as well as the joint-adjacent parts of the bone. If cartilage and/or joint are excessively damaged, which may also be due to or resulting from fractures, a joint replacement may be required. The damaged articular cartilage and possibly also parts of the bone are removed where necessary. A joint replacement, usually made of metal, is inserted into the joint and assumes as much as possible the function of the damaged structures, i.e. cartilage and bone.

The object of the present invention is to provide a joint replacement or a surface replacement implant, in particular for the elbow joint with the distal humerus and the proximal radius. Furthermore, a set and a method are to be provided.

The object according to the present invention is achieved by an elbow joint replacement having the features of claim 1. It is further achieved by a set having the features of the claim 25 and by a method having the features of claim 26.

In particular, a partial elbow joint replacement is proposed by the present invention.

The elbow joint replacement comprises at least one segment, or exactly one segment, in particular a shell-like segment, dome-like segment or a differently curved segment, having an inner contour which is completely, or at least in section thereof, concave. The segment is configured or provided in order to be arranged on or at at least one cartilage structure and/or bone structure of a patient's joint.

The segment, herein referred to purely by way of example as shell-like, comprises a lateral section and a medial section (or a first section and a second section, wherein the first section lies laterally to the second section after implanting the elbow joint replacement). Both sections are arranged adjacent to each other (with or without contacting one another or being in an indirect or direct transition) along a longitudinal direction of the shell-like segment.

An outer contour of the segment comprises in longitudinal direction of the elbow joint replacement or of the segment at least one or exactly one inflection point. The inflection point is respectively optional. It does not limit the scope of the present invention.

The set according to the present invention encompasses at least one elbow joint replacement according to the present invention.

It further encompasses at least one tool for processing the bone structure. The tool is preferably designed or configured to adapt the bone structure to an inner contour of the elbow joint replacement.

The tool (or instrument) may be a milling tool, a grater, a shaver or another tool, in particular a cutting tool.

"Processing" of bone structures may be understood as milling, grating, removing, etc. preparing and/or adapting.

The set according to the present invention serves the processing of cartilage structures and/or bone structures for the preparation of an implantation of, in particular a partial elbow joint replacement according to the present invention.

It encompasses inserting a wire, like a drill wire, a K-wire or a Kirschner-wire into the bone in the joint region.

It further encompasses inserting a tool for the processing of the bone structure using the wire. The tool can therefore be threaded through the wire.

Finally, the set according to the present invention encompasses removing the tool from the joint region after the processing.

In all of the embodiments herein, the use of the expression "may be" and "may have" etc. is synonymous to "is preferably" or "has preferably," etc. respectively, and is intended to illustrate an embodiment according to the present invention.

Whenever numerical words are mentioned herein, the person skilled in the art will comprehend them as indications of numerical lower limits. Unless it leads the person skilled in the art to an evident contradiction, the person skilled in the art will comprehend the specification for example of "one" as encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and applies herein to all used numerical words.

Advantageous developments of the present invention are each subject-matter of the dependent claims and embodiments as well as of the figures.

When an elbow joint replacement is mentioned herein, it is not intended to be limiting. In some embodiments according to the present invention, the implant is namely configured or designed to be used as an elbow joint replacement. In other embodiments according to the present invention, the implant is however configured or designed to be used for other joints than the elbow joint.

Arranging the segment on or at at least one bone structure of the patient may take place indirectly (if there are remains of residual cartilage) or directly (without cartilage remains).

In some exemplary embodiments according to the present invention, the subject-matters according to the present invention comprise one or several of the herein described features in any combination, unless such a combination is recognized by the person skilled in the art as technically impossible.

In some exemplary embodiments according to the present invention, an inflection point of the elbow joint is understood to be a point of the elbow joint (approximately on its outer surface or outer contour), at which the course of the outer contour (for example, when viewing the elbow joint replacement in a longitudinal section or from the side) changes or at which another graph associated with the elbow joint replacement changes its curvature characteristic: The course or the graph changes here either from right into a left curve or vice versa.

In some exemplary embodiments according to the present invention, the inflection point is to be understood in accordance with its meaning in the context of the mathematical curve discussion.

In some exemplary embodiments according to the present invention, the inflection point is that point on the outer contour or on the graph at which the curvature of the outer contour or the graph changes its sign.

In some exemplary embodiments according to the present invention, the inflection point is that point at which the curvature of the outer contour or of the graph changes from concave to convex.

In some exemplary embodiments according to the present invention, the inflection point lies in a transition region between the lateral section and the medial section.

According to the present invention, a partial elbow joint replacement is when only a part or a side (lateral, medial, proximal, distal) of a bone associated with the joint is replaced. If for example only a part or a side of the elbow joint is worn or damaged, it may suffice to renew only the worn or damaged part of the joint. If this is the case, then only a partial joint replacement or a one-sided surface replacement is mentioned. Only a part of the end of the bone associated with the joint, such as the humerus, is replaced; the joint replacement does not affect the entire medial-lateral extent of the bone, such as the humerus. The joint replacement may have a less longitudinal extension than the joint surface. The longitudinal extension may be less than the width of the bone.

A total joint replacement is mentioned by the present invention when the distal humerus, in particular only the complete surface of the capitulum without trochlea, and the proximal radius or radial head is replaced by implants.

Furthermore, a joint replacement may be mentioned by the present invention when previously implanted implants of the distal humerus and/or of the proximal radius are replaced by other or further or new implants.

In some exemplary embodiments according to the present invention, the terms "lateral" and "medial" refer to the placement of the elbow joint replacement on the patient in the implanted condition as intended. "Lateral" and "medial" are understood as one understands these terms in relation to the patient.

In some exemplary embodiments according to the present invention, the inner contour of the segment is the inner side, or concave side, or the side facing the bone or contacting it after implantation indirectly or directly.

In some exemplary embodiments according to the present invention, the surface facing the joint surface during use of joint replacement, a polished, abrasion-proof and thus tribologically-optimized surface.

In some exemplary embodiments according to the present invention, the inner side, facing the bone during use of the joint replacement, comprises material characteristics and/or surface characteristics which are regarded as osteoinductive/osteointegrative by the person skilled in the art. The osteoinductivity may be achieved or obtained or promoted by a micro-macrostructure and/or interconnecting macrostructure, for example by a suitable selection of surface material.

In some exemplary embodiments according to the present invention, a fixed connection is provided between the treated bone bearing and the implant during use of the joint replacement. This may be achieved through different anchoring principles, for example by mandrel, comb, screw connection, angularly stable screw connection. In addition, the connection may be biologically promoted by an interaction between the bone and the implant, which gradually develops and may promote long-term stability.

In some exemplary embodiments according to the present invention, the joint replacement comprises resorbable materials, in particular facing the bone bearing, that degrades after implantation of the joint replacement and which promotes stability.

In some exemplary embodiments according to the present invention, the joint replacement or the segment is made of a biocompatible metal alloy (CoCr-alloy or the like.).

In some exemplary embodiments according to the present invention, the material is a biocompatible metal, a ceramic, a plastic or a combination thereof.

In some exemplary embodiments according to the present invention, the metal is CoCrMo-alloy, and/or a ceramic e.g. a zirconium oxide or an aluminum oxide ($Al_2O_3$).

In some exemplary embodiments according to the present invention, the plastic is PEEK and/or UHMWPE (ultrahigh molecular weight polyethylene). The plastics, in particular PEEK, may be fiber-reinforced, for example through carbon fibers and/or glass fibers.

In certain exemplary embodiments according to the present invention, the material is a carbon fiber-reinforced plastic (in short: CFP)

In some exemplary embodiments according to the present invention, the elbow joint replacement on the side of the humerus and a joint replacement on the side of the radius form a slide pairing.

In some exemplary embodiments according to the present invention, metal-plastic or ceramic-ceramic is provided for the joint replacement as material pairing or slide pairing. This advantageously contributes to the reduction, prevention or avoidance of abrasion when using the joint replacement. This may also contribute to the longevity of the elbow joint replacement, the reduction of infection risk or occurrence of allergic reactions by the patient.

In some exemplary embodiments according to the present invention, the joint replacement or a part thereof is designed to serve as partial or—preferably—total replacement of the radial head (caput radii). To obtain the desired joint mechanics, sizes and proportions are based preferably on anatomical analysis.

In some exemplary embodiments according to the present invention, the joint replacement comprises a plate shape or a wheel shape, for example when viewing the joint replacement from the side.

In some exemplary embodiments according to the present invention, the joint replacement comprises at least one or exactly one indentation or recess depth on its surface or outer contour, in particular on an upper surface thereof.

The indentation or recess depth is preferably adapted to the diameter and/or the height of the head (varies with implant sizes).

In some exemplary embodiments according to the present invention, the outer wall of the head of the joint replacement is curved. This advantageously enables the joint replacement to fit into or on the joints surface of the ulna.

In some exemplary embodiments according to the present invention, the joint replacement comprises a coating, preferably for promoting osteointegration, on the part facing the bone. The coating may be applied by pure titanium—plasma spray with a layer thickness of 40-50 μm and a roughness of about 7 μm. The coating may be hydroxyapatite (=bone cement) or the like. The coating may be applied on all embodiments according to the present invention, for example on the distal humerus (capitulum implant) or on the proximal radius (radial head implant).

In some exemplary embodiments according to the present invention, the joint replacement comprises an anchoring device.

In some exemplary embodiments according to the present invention, the anchoring device of the joint replacement comprises, in particular at the proximal radius, at least one tip or at least one end section which lies most distal after implantation. The tip or end section may be rounded, which counteracts undesirable damage to the bone (e.g. the radius) during implantation and particularly during insertion.

In some exemplary embodiments according to the present invention, the anchoring device of the joint replacement comprises, in particular at the distal humerus, at least one tip or at least one end section which lies most proximal after implantation. The tip or end section may be rounded, which counteracts undesirable damage to the bone (e.g. the humerus) during implantation and particularly during insertion.

In some exemplary embodiments according to the present invention, the anchoring device of the joint replacement comprises lateral indentations for promoting osseointegration. They enable the bone to grow into them, making the implantation more stable by forming undercuts.

In some exemplary embodiments according to the present invention, the anchoring device is designed as tapered shaft, trapezoidal shaft, wedge, barb screw fixation or the like.

In some exemplary embodiments according to the present invention, the anchoring device is embodied as a plurality of flexible, elastic or bendable spikes, preferably with a re-set or restore property. This enables the spikes to adapt to the geometry or the surface upon insertion into the medullary space. They are bent to the inside or they bend to the inside during implantation. By pushing against the bone to the outside due to their flexibility and due to the stress caused by their bending, they contribute to the stability of the anchoring.

In some exemplary embodiments according to the present invention, the spikes or the tips comprise barbs that bury themselves into the bone, which may additionally protect against undesired translation in the axial or radial direction, or generally against a position change, and against an undesirable rotation.

In some exemplary embodiments according to the present invention, the joint replacement comprises a wedge denoted herein as short wedge. Although the greatest contribution to stability is caused or achieved by resting the head of the joint replacement on the cortical portion of the radial neck, the short wedge is inserted into the spongy bone or, if still present, in the medullary space to increase the stability. Due to the little height of the wedge, the joint needs to be spread only slightly for implantation, which may serve to preserve the soft parts/ligaments and help maintain the natural joint stability.

The wedge may have holes or openings which may be used for the ingrowth of the bone and thus for the long-term stability of the implant.

The wedge may have a T-shape in the cross section. This enables high stability of the component. In addition, it may enable a filigree design.

The lateral side of the wedge may be rounded to the inside. Hence, the implant may—without or with only little spreading of the joint and/or stretching the joint line—be inserted.

The medial side of the wedge may be wider compared to the lateral side. It may be rounded. Therefore, the greatest possible contact area with the bone may be achieved.

The rounding of the tip of the wedge may advantageously contribute to the fact that the tip does not undesirably cut the bone and the bone is not additionally damaged. A plateau is provided facing the head so that the wedge may be supported on both sides on the bone.

The wedge may have a height of 10 to 20 mm, preferably a height of about 15 mm (possibly variable with different head sizes).

In some exemplary embodiments according to the present invention, the joint replacement comprises materials which include the so-called Shape Memory Alloys (in short: SMA), or memory metal, such as e.g. Nitinol (in short: NiTi), cobalt chromium, composites, X-ray transparent materials and/or ceramic.

In some exemplary embodiments according to the present invention, the joint replacement is machined and/or produced by a casting, forming or additive process.

The implant form may be cylindrical (advantageous because therethrough one has a simpler bone bearing processing and the implant may be inserted) to the direction of the bone (implant inner contour), triangular (see the following elaborations related thereto), cylindrical with a medially or laterally conical course (advantageous, as there is no translation in direction of the implant's longitudinal axis). But it may also have a barrel shape or a form adapted to the joint surface (advantageous by under cutting).

In some exemplary embodiments according to the present invention, the extension of the lateral portion (or of at least portion thereof or all portions thereof) in the radial direction is greater than the extension of the medial portion (or of at least a portion or all portions thereof) in the radial direction. Likewise, the extension of the lateral portion (or at least a partial portion or all partial portions thereof) in the radial direction may be designed to be initially smaller, then increasingly larger up to an apex point, and then again flatly smaller.

In some exemplary embodiments according to the present invention, the shell-like segment comprises no closed circumference in the circumferential direction of the segment. The circumferential direction is perpendicular to the longitudinal direction and/or perpendicular to the radial direction of the segment.

In some exemplary embodiments of the implant of the distal humerus according to the present invention, the thickness of the wall of the shell-like segment is between 1 mm and 5 mm, in particular between 2 mm and 3 mm. Preferably, this applies to each wall section; preferably, no wall section in such embodiments is thicker than indicated supra.

In some exemplary embodiments according to the present invention, the segment comprises, at least in sections thereof, an outer contour and/or an inner contour which has been adapted to be patient-specific in a preoperative planning stage via a computer imaging. In some exemplary embodiments according to the present invention, the outer contour is preferably such that it is identical or modeled to the congenital course of a corresponding bone part of an elbow joint of a patient.

In some exemplary embodiments according to the present invention, the shell-like segment comprises a rough inner contour surface. Preferably, the surface roughness is an average roughness $R_a$ of about 7 μm. Such roughness, as well as macroscopic surface characteristics such as e.g. interconnecting surface structure, may contribute or lead to improved osseointegration.

In some exemplary embodiments according to the present invention, the inner contour of the segment is designed, corresponds to or extends in the longitudinal direction analogously to the outer contour of the segment.

In some exemplary embodiments according to the present invention, the inner contour of the segment comprises in the longitudinal direction at least one inflection point.

In some exemplary embodiments according to the present invention, the inner contour of the lateral section of the segment comprises a concave, non-cylindrical contour. The inner contour of the medial section of the segment comprises a cylindrical contour in longitudinal direction.

In some exemplary embodiments according to the present invention, the inner contour of the lateral section of the segment comprises a concave, non-cylindrical contour. The inner contour of the medial section of the segment comprises a convex contour curved to the inside in longitudinal direction.

In some exemplary embodiments according to the present invention, the inner contour of the lateral section of the segment comprises a concave, non-cylindrical contour. The inner contour of the medial section of the segment comprises a contour curved to the inside in longitudinal direction.

In some exemplary embodiments according to the present invention, the inner contour of the lateral section of the segment comprises a cylindrical contour and the inner contour of the medial section of the segment comprises a convex contour in longitudinal direction or a convex contour in circumferential direction.

In some exemplary embodiments according to the present invention, the shell-like segment comprises at its lateral end-face section a fixing unit which is configured or designed to fix the shell-like segment on or to the bone via said fixing unit.

In some exemplary embodiments according to the present invention, the fixing unit comprises, or consists of, one or at least one screw.

The shell-like segment may comprise a through-opening provided for the insertion of the screw or a thread for fixation on the bone.

The shell-like segment may comprise a through-opening provided for the insertion of a thread for fixation of tendons, ligaments or other tissue structures.

In some exemplary embodiments according to the present invention, the fixing unit comprises—of each—, or consists of, at least one tab, one web and/or one strut or the like as a screw holder.

In some exemplary embodiments according to the present invention, the fixing unit is fixable or provided to be fixable in the bone in longitudinal direction, parallel or substantially parallel to the longitudinal direction.

In some exemplary embodiments according to the present invention, the segment or sections thereof are made of a—preferably biocompatible—metallic and/or a ceramic material and/or a composite material and/or polymer material (e.g. PEEK (polyetheretherketone).

In some exemplary embodiments according to the present invention, the segment comprises at its inner side at least one fixing element for anchoring the elbow joint replacement in a bone structure.

In some exemplary embodiments according to the present invention, the inner side is the inner surface of the segment, in particular of the implant of the distal humerus.

In some exemplary embodiments according to the present invention, the longitudinal axis extends parallel to an axis of rotation of the elbow joint; in the implanted condition of the elbow joint replacement, it is an axis of rotation of the elbow joint.

In some exemplary embodiments according to the present invention, the outer side of a further segment is shaped such that it is conformal or congruent to a surface of a proximal ulna of the elbow joint.

In some exemplary embodiments according to the present invention, the elbow joint replacement ends laterally with an inlet or entrance or opening plane or wall which lies in a plane at an angle relative to the longitudinal axis of the elbow joint replacement.

In some exemplary embodiments according to the present invention, the angle is in a range from 25° to 45°, preferably between 30° and 40°, and is particularly preferably 35°, preferably exactly or approximately 35°.

In some exemplary embodiments according to the present invention, the elbow joint replacement further encompasses a radial prosthesis or partial radial prosthesis, in particular for the radial head (as a radial head implant) or parts thereof. This may comprise an anchoring device and/or a coating.

In some exemplary embodiments according to the present invention, the method further encompasses inserting the partial elbow joint replacement with the aid of a wire, a K-wire (the K-wire may be referred to as Kirschner wire) or a drill wire, herein referred to in short as wire.

The wire is inserted preferably laterally into the axis of rotation or into a rotation section of the implant of the distal humerus, preferably guided as closely and as parallel to the axis of rotation as possible.

A tool, such as a miller or a shaver, is pushed by the wire and slid over the surface of the bone which is to be processed with the tool.

The tool has a tissue protector which, in use, lies between soft tissue or tissue which is not to be treated with the tool, and the bone to be processed.

The tool also preferably has a rotating tool section whose outer contour is either spherical, or again preferably congruent with the outer contour of the bone which is to be obtained using the tool. The rotation axis of the tool is preferably parallel to the rotation axis of the joint during use.

The tool or a holder for the tool may have a through-opening for the insertion of the aforementioned wire. The tool may then be moved around the axis of rotation in a controlled manner. The bone is removed by this movement.

According to the present invention, the aforementioned tool may be used alone. However, the present invention also encompasses two or multi-stage processes or procedures in which, for example, a cylindrical miller is inserted, e.g. first a cylindrical miller is introduced, e.g. via the wire as described above. Subsequently, the individual, in any case non-cylindrical miller, may be inserted giving the bone the desired non-cylindrical outer contour. Such a multi-stage process requires a comparatively low working height for the tool in the joint region. The joint line needs less expanding than in the process described above, in which exactly one tool is used. This may imply a preservation of the soft tissue parts.

In some exemplary embodiments according to the present invention, the method further encompasses removing the drill wire and optionally inserting a fixing element for anchoring the elbow joint replacement into the bone structure.

In some exemplary embodiments according to the present invention, the elbow joint replacement comprises a longitudinal direction, a cross section and a circumferential direction.

In some exemplary embodiments according to the present invention, the elbow joint replacement comprises two medial or lateral ends or medial or lateral end regions which terminate in the longitudinal direction of the elbow joint replacement. It further comprises at least one or exactly one curved section which is curved in the circumferential direction of the elbow joint replacement. Alternatively, the elbow joint replacement consists of the section which is curved in the circumferential direction of the elbow joint replacement. The curved section may be the above-mentioned segment of the elbow joint replacement.

In some exemplary embodiments according to the present invention, the curved section is exclusively curved, e.g. exclusively convex or exclusively concave.

In some exemplary embodiments according to the present invention, the elbow joint replacement comprises the smallest curvature in a middle region in the longitudinal direction of the elbow joint replacement.

In some exemplary embodiments according to the present invention, the curved section comprises its greatest thickness in a middle region in the longitudinal direction of the elbow joint replacement.

In some exemplary embodiments according to the present invention, the elbow joint replacement comprises a collar section which is medial to the curved section.

In some exemplary embodiments according to the present invention, the inner side and/or the outer side of the collar section is medially wider than the lateral, or wherein the inner side and/or the outer side decreases along the longitudinal axis from medial to lateral.

In some exemplary embodiments according to the present invention, the joint replacement terminates medially and/or laterally with an entrance/opening plane or wall being perpendicular to the longitudinal axis.

In some exemplary embodiments according to the present invention, the elbow replacement or the curved section comprise an upper side and a bottom side in the longitudinal direction of the joint replacement, and wherein the upper side of the joint replacement and/or the curved section is longer than its bottom side.

In some exemplary embodiments according to the present invention, the curved section is formed on its inner side such that it conforms to a capitulum surface of a distal humerus of the elbow joint, and/or to an olecranon fossa of a rear surface of distal humerus of an elbow joint or is congruent with it.

In some exemplary embodiments according to the present invention, the curved section is formed at its inner side such that it conforms to, or congruent with, another distal humeral joint surface, particularly the medial region beyond the capillary of the humerus of the elbow joint.

In certain exemplary embodiments according to the present invention, the elbow joint replacement is completely or partially prepared or configured to be fixed in the bone structures using bone cement. In this, the surfaces of the implants, or sections thereof, may be coated or not coated, surface-treated or not surface-treated, smooth or not smooth for the distal humerus, in particular the capitulum implant and/or for the proximal radius. In particular, special anchoring devices of the implants such as, e.g., shafts of different shapes, wedges or hooks may have the described surfaces.

Some or all embodiments according to the present invention may comprise one, several or all of the advantages mentioned above and/or in the following.

The joint replacement is characterized through the most congruence with the native form of the capitulum. The different curvature radii of the joint surface are advantageously imitated (at least two different radii) on the joint replacement. Due to the shape of the adjacent joint surface at the radius and the form at the distal humerus (direction trochlea), it is also advantageous if the joint surface terminates medially with a collar section. On the lateral side, the shape may be determined distally by the taper by an angle. The transfer of this angle to the implant shape may have a positive effect on the adjacent ligaments. An increased biomechanical stability may be achieved by the shape and dimensions of the implant. Ligaments are preserved during implantation by the possibility of soft tissue-protecting and/or minimally invasive insertion and by the position and dimensions.

The present invention is exemplarily described in the following based on the accompanied figures in which identical reference numerals refer to the same or similar components. In each of the schematically simplified figure, the following applies:

FIG. 1 *a-e* show a capitulum implant of a partial elbow joint replacement in a first exemplary embodiment;

FIG. 2 shows the morphology of bone structures of a distal humerus region;

FIG. 3 *a-d* show a capitulum implant of a partial elbow joint replacement according to the present invention which is virtually implanted on a capitulum of a distal humerus region;

FIG. 4 *a-b* show a capitulum implant of a partial elbow joint replacement according to the present invention in a second exemplary embodiment;

FIG. 5 *a-c* show a capitulum implant of a partial elbow joint replacement according to the present invention in a third exemplary embodiment;

FIG. 6 *a-c* show a capitulum implant of a partial elbow joint replacement according to the present invention in a fourth exemplary embodiment;

FIG. 7 *a-c* show a capitulum implant of a partial elbow joint replacement according to the present invention in a fifth exemplary embodiment;

FIG. 8 *a-b* show a capitulum implant of a partial elbow joint replacement according to the present invention in a sixth exemplary embodiment;

FIG. 9 *a-c* show a capitulum implant of a partial elbow joint replacement according to the present invention in a seventh exemplary embodiment;

FIG. 10 *a-b* show a capitulum implant of a partial elbow joint replacement according to the present invention in an eighth exemplary embodiment;

FIG. 11 *a-b* show a capitulum implant of a partial elbow joint replacement according to the present invention having a conical shaft as an anchoring device;

FIG. 12 *a-c* show a capitulum implant of a partial elbow joint replacement according to the present invention having a trapezoidal shaft as an anchoring device;

FIG. 13 *a-c* show a capitulum implant of a partial elbow joint replacement according to the present invention having a wedge as an anchoring device;

FIG. 14 *a-c* show a capitulum implant of a partial elbow joint replacement according to the present invention having a barb as an anchoring device;

FIG. 15 *a-c* show a capitulum implant of a partial elbow joint replacement according to the present invention having a flap for fixing screws as an anchoring device;

FIG. 16 *a-b* show a capitulum implant of a partial elbow joint replacement according to the present invention having a flap for fixing screws which is fixed by a hinge as an anchoring device;

FIG. 17 *a-b* show a radial head implant of a partial elbow joint replacement according to the present invention;

FIG. 18 *a-b* show a radial head implant with a wedge-formed mandrel as an anchoring device of an elbow joint replacement according to the present invention;

FIG. 19 *a-c* show a radial head implant with a wedge as an anchoring device of an elbow joint replacement according to the present invention;

FIG. 20 *a-b* show a radial head implant with a further wedge as an anchoring device of an elbow joint replacement according to the present invention;

FIG. 21 *a-c* show a radial head implant with a further wedge as an anchoring device of an elbow joint replacement according to the present invention;

FIG. 22 *a-c* show schematically the individual steps for introducing a radial head implant into the proximal radius;

FIG. 1a shows a perspective view of a first exemplary embodiment of a capitulum implant 100 of a partial elbow joint replacement 1000 for an elbow joint. The exact arrangement of the capitulum implant 100 as surface replacement of the capitulum humeri at the lateral section of the distal humerus is illustrated in the FIGS. 3a to 3d and is described with respect thereto.

Figure 2:
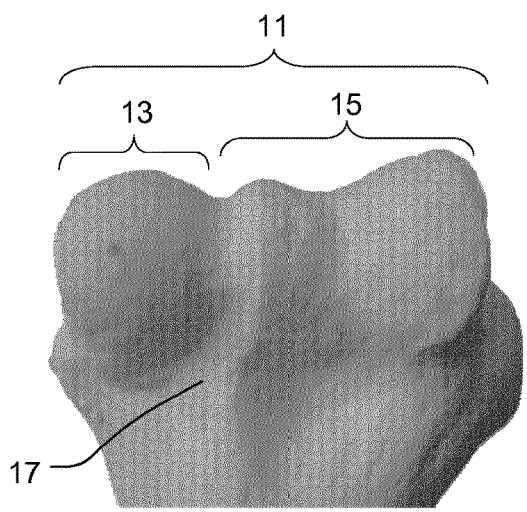

The capitulum implant 100 is in the following referred to as implant 100 in a simplified way.

The capitulum implant 100 may be designated as a shell-like segment 100.

The implant 100 is shell-like shaped and has a curved outer surface contour 1 (outer contour) and an inner surface contour (inner contour) 3. The implant 100 is optionally not closed neither on a lateral end face 5 nor on a medial end face 7 thereof.

The thickness of the wall of the implant 100, i.e. the distance between the outer surface and inner surface of the implant 100, is in this first embodiment constant through all the sections of the implant 100.

In the circumferential direction u (see FIG. 1c), the shell-like form is optionally also not closed, as this is described in more detail in the following figures.

The longitudinal direction of the implant 100 is denoted with x.

FIG. 1b shows the implant 100 of FIG. 1a in a side-view in which an inflection point 9 is visible in the outer surface seen in longitudinal direction x. At this point the inflection point 9 is the transition point between the approximately spherical shape in the region of the capitulum humeri (on the lateral side of the implant) and the medially adjoining region of the implant 100 in the direction of the trochlea humeri (see FIGS. 2 and 3).

The inner contour 3 of the implant 100 is approximately anatomically formed, corresponding to the natural joint surface, so that as little bone substance as possible has to be removed or milled off before the implant 100 is implanted. This allows an improved blood circulation of the bone compared to procedures where more bone substance is removed.

Further, the view in FIG. 1b shows that the medial end face 7 closes or terminates perpendicular to the longitudinal direction x by way of example, whereas the lateral end face 5 closes with a curve-form, which is described in more detail in the following figures.

FIG. 1c shows a further perspective view of the implant 100 of FIG. 1a obliquely from the top on the curved outer surface 1 and the medial end face 5.

FIG. 1d shows the implant 100 of FIG. 1a in a side view in which the implant 100 relative to the view in FIG. 1b is tilted by 180 degrees about a transverse axis (in radial direction r) and rotated by 90 degrees about its longitudinal axis x. The medial end face 7 is arranged on the left, the lateral end face 5 on the right.

In this view, the form of the lateral end face 5 is clearly visible. This form is adapted to the lateral, anatomical end of the capitulum humeri (see FIGS. 2 and 3).

Together with the view in FIG. 1e, individual exemplary dimensions are specified for the dimensioning of different implant sizes. These exemplary dimensions result from the measurements or determinations carried out by computer tomography (CT images) of about patient data sets of distal humeri.

FIG. 1e shows a view of the implant 100 of FIG. 1d tilted by 90 degrees around the radial axis r to the left and rotated around the longitudinal axis x The parameters measured or determined by means of the patient data are categorized in the following exemplary implant sizes. The abbreviations for the implant sizes are as follows:

|  | S | M | L | XL |
|---|---|---|---|---|
| $X_1$ [mm] | 17.65 | 20.15 | 22.65 | 25.15 |
| $X_2$ [mm] | 10.18 | 11.51 | 12.85 | 14.19 |
| $X_3$ [mm] | 6.38 | 7.34 | 8.30 | 9.27 |
| $R_1$ [mm] | 8.60 | 9.80 | 11.00 | 12.20 |
| $R_2$ [mm] | 7.08 | 7.89 | 8.70 | 9.51 |
| $R_3$ [mm] | 7.63 | 8.58 | 9.52 | 10.47 |
| $R_4$ [mm] | 10.78 | 11.59 | 12.39 | 13.20 |
| $R_5$ [mm] | 3.93 | 4.06 | 4.18 | 4.31 |
| α [degree; °] | 35 | 35 | 35 | 35 |
| $β_1$ [degree; °] | 120 | 120 | 120 | 120 |
| $β_2$ [degree; °] | 80 | 80 | 80 | 80 |

S—Small;
M—Medium;
L—Large;
XL—Extra Large

FIG. 2 shows the morphology of bone structures of a distal humerus region. Shown are in particular the elbow joint 11 (or the portions of the humerus thereon) with the capitulum 13 and the trochlea 15, which build the distal end region of the humerus 17. For example, if the elbow joint is damaged or injured in the region of the capitulum 13, the surface of the capitulum 13 can be replaced by a partial elbow joint replacement 1000 according to the present invention as shown in FIGS. 3a to 3d, for instance after milling of surface layers of bone structures.

Figure 3A:
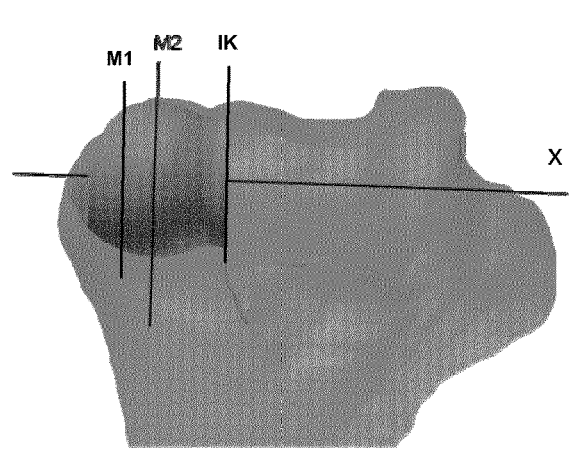

FIG. 3a shows a capitulum implant 100 of a partial elbow joint replacement 1000 according to the present invention which is virtually implanted on the capitulum of a distal humerus region. The marked cutting or intersecting planes M1, M2 and IK are e.g. measurement planes which refer to characteristic planes in the imaging examinations of the patient. The measuring results may provide indications for the surgeon concerning the size of the implant 100 to be selected for implanting a partial elbow joint replacement 1000 (see description to FIG. 1, implant sizes: S/M/L/XL). The longitudinal direction x may be referred to as rotation axis. The rotation axis may be related to the implant 100 as well as to the trochlea and/or capitulum. The marked cutting planes M1, M2 and IK are arranged perpendicular (or orthogonal) to the rotation axis.

Figure 3B:
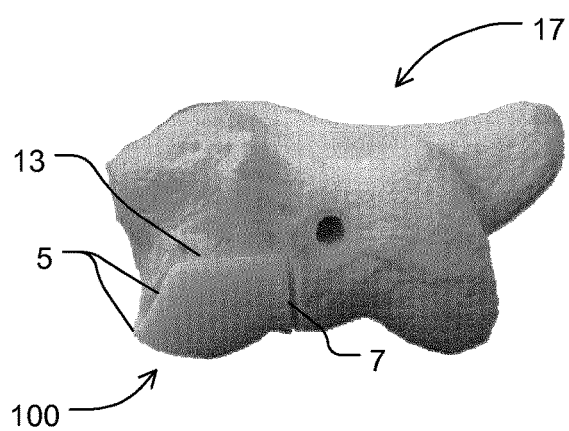

FIG. 3b shows a prototype of the implant 100, placed on a model of a distal humerus made of plastic, and an elbow joint. The implant 100 is placed on the capitulum 13 of the distal humerus 17. In this view it is easy to see how the lateral end region 5 and the medial end region 7 of the implant 100 adapt themselves to the adjacent bone structures or attach to them.

Figure 3C:
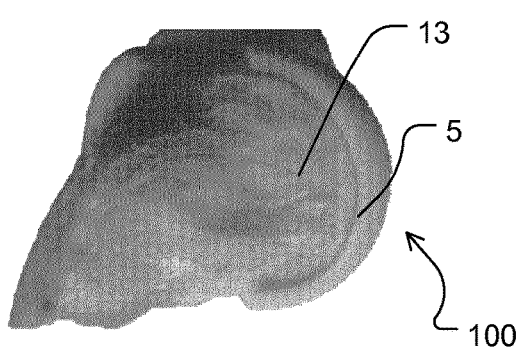

FIG. 3c shows the view of FIG. 3b rotated or tilted by 90 degrees to the right. The circumferential angle around the rotation axis or the longitudinal axis x is larger than 180 degrees, analogous to FIG. 1e, in which the circumferential angle measures 200 degrees (ß$_1$: 120 degree+ß$_2$:80 degrees), so that the implant 100 to be placed on the capitulum 13 must be slightly expanded before it can be attached to the capitulum 13 in a form-closure manner.

Figure 3D:
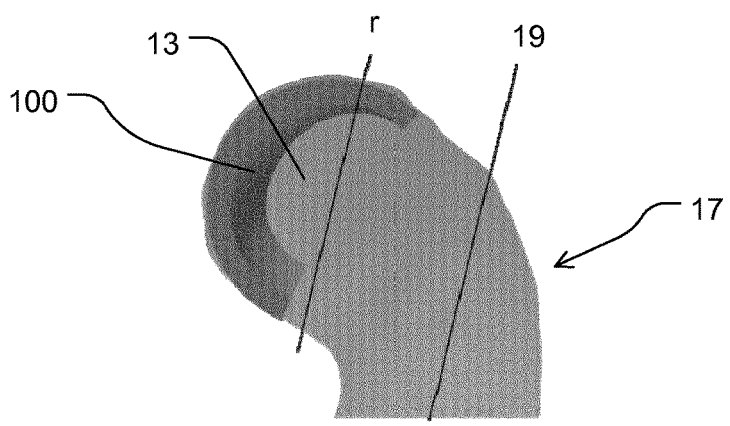

FIG. 3d shows a virtual arrangement of the implant on the capitulum 13. Shown in this view are the parallel axes of a longitudinal axis 19 of the humerus 17, in which the longitudinal axis is in particular the shaft axis 19 of the humerus 17, and an axis in radial direction r of the implant 100, which is at the same time a radial direction r of the capitulum. The radial direction r is perpendicular or orthogonal to the rotation axis, or to the longitudinal axis x, of the implant 100.

FIG. 4a shows a capitulum implant 100 of an elbow joint replacement according to the present invention 1000 in a second exemplarily embodiment. Compared to the form and contour of the first embodiment of the implant 100 from FIGS. 1a to 1c, the second embodiment comprises a cylindrical inner contour 21 in the medial end section 7. A cylindrical inner contour 21 may simplify a processing of the bone structure, e.g. by using a suitable cutting miller, compared to a continuously anatomically formed contour (see FIGS. 1a to 1c). An anatomically formed contour may imply a greater effort and a longer processing time, also of the corresponding bone structures, due to concave contours and to possible freeform surfaces.

A securing against a translational displacement of the implant 100 along the x-direction after a positioning on the capitulum 13 may be achieved by the remaining shape of the concave inner contour (lateral side). The securing is thus independent of the inner contour shape in the medial end region 7. However, an anatomical shape (see FIGS. 1a to 1c) may advantageously additionally block and protect against a displacement along the x-direction.

The wall thickness of the implant 100 may in the area of the cylindrical inner contour 21 be greater and may possibly comprise an increased stability against an anatomically formed inner contour—at least in sections of the inner contour.

A lateral sliding of the implant 100 of the second embodiment with regard to FIG. 4a and FIG. 4b (in FIG. 4a from left to right) onto the capitulum 13 may be made easier or even possible for the first time due to the cylindrical inner contour 21, compared to the anatomical shape according to FIGS. 1a to 1c. Due to the undercut in the medial end region 7, the anatomical shape may prevent or at least hinder a lateral sliding.

An anatomically-shaped inner contour (see FIG. 1a to FIG. 1c) may reduce and minimize the amount of a necessary bone resection (removal of bone structures for adaptation to the implant shape) compared to the cylindrical inner contour 21.

FIG. 4b shows a perspective view of the second embodiment of the implant 100.

FIG. 5a shows a capitulum implant 100 of an elbow joint replacement 1000 according to the present invention in a third exemplary embodiment. In this third embodiment, the inner contour 3 (or inner surface form) is continuously, i.e. from medial 7 end region to lateral end region 5, cylindrical.

A cylindrical inner contour may simplify and facilitate the processing of the bone structure on which the implant 100 is placed. A cylindrical shape is usually easier to achieve, for example by milling, than an anatomical contour as shown in FIG. 1a to FIG. 1c. However, an increased volume of removed bone structures may be undesirable for other reasons (for example an increased bone stability as the basis for the stability of the implant 100). Therefore, minimum internal radii may purely exemplarily be given for the cylindrical inner contour which refer to the table in FIG. 1e with respect to the other dimensions (see above). These minimum internal radii are intended to ensure a sufficient bone substance for fixing and stabilizing the implant 100. The values given in the following are to be understood purely as an example. For the implant category S (Small), a minimum internal radius of 5.4 mm can be given, for M (Medium): 6.0 mm, for L (Large): 6.6 mm and for XL (Extra Large): 7.2 mm. Thus, the wall thicknesses of the implant, in particular in the stressed area (through natural arm movements and the resulting forces on the elbow joint), are approximately between 3.2 mm (for S) and 5 mm (for XL).

A cylindrical inner contour may simplify or even allow lateral sliding of the implant 100 on the capitulum 13, in particular at a circumferential angle ß being greater than 180 degrees (see FIG. 1e).

However, a cylindrical inner contour may not ensure or may less reliably ensure securing and/or anchoring against translational movements along the axis of rotation (longitudinal axis x) as well as a rotation of the implant 100 and the axis of rotation (in circumferential direction u) without additional fixations using screws, or anchoring the implant 100.

FIG. 5b shows a side view and FIG. 5c shows a perspective view of the third exemplary embodiment of the implant 100. FIG. 5b clearly illustrates that the circumferential angle ß (see the description of FIG. 1e) is greater than 180 degrees.

FIG. 6a shows a capitulum implant 100 of an elbow joint replacement 1000 according to the present invention in a fourth exemplary embodiment. Compared to the third embodiment, the fourth embodiment comprises a cylindrical landing 23 shifted to the inside and arranged in the circumferential direction u. The shifted cylindrical landing 23 may be referred to as a section having a cylindrical step having a smaller radius compared to the cylindrical form arranged further laterally. The descriptions and discussions related to FIG. 5a apply largely analogously to FIG. 6a. However, the implant 100 of the fourth embodiment may not be shifted laterally in the longitudinal direction x onto the capitulum 13, but must be placed from the front (anterior). For this reason, it is necessary that the circumferential angle ß (see FIG. 1e) is max. 180 degrees. After placement on the capitulum 13, the implant 100 is secured against displacement (translational movement in x direction) on the capitulum 13 of the elbow joint.

FIG. 6b shows a side view rotated approximately 90 degrees around the longitudinal axis x, and FIG. 6c shows a perspective view of the fourth exemplary embodiment of the implant 100.

FIG. 7a shows a capitulum implant of a partial elbow joint replacement 1000 according to the present invention in a fifth exemplary embodiment. This embodiment is very similar to the fourth embodiment (FIG. 6), wherefore the description and discussion related to FIG. 6 apply analogously also here. Only the cylindrical landing 23 of FIG. 6a which is shifted to the inside is embodied in FIG. 7a in a semicircular shape. The step which arranged to the inside may be referred to as semicircular notch 25. This exemplarily has an effect on the form of the processing of bone structure in this region and requires a modified manufacturing of the implant 100.

The notch 25 may alternatively to the semicircular shape comprise another form.

FIG. 7b shows a side view rotated approximately 90 degrees around the longitudinal axis x and FIG. 7c shows a perspective view of the fifth exemplary embodiment of the implant 100.

FIG. 8a shows a capitulum implant 100 of a partial elbow joint replacement 1000 according to the present invention in a perspective view in a sixth exemplary embodiment. Compared to the fourth embodiment (FIG. 6) and fifth embodiment (FIG. 7), the sixth embodiment comprises in the longitudinal direction x two notches 27 which are arranged on the opposite circumference, shifted to the inside and semicircular. The notches 27 are respectively arranged on both end sections of implant 100 which are not closed in the circumferential direction u. In particular, FIG. 8b clearly illustrates that the circumferential angle ß is greater than 180 degrees, so that the implant can either be shifted on the lateral side of the capitulum 13 or placed on the radial side by (elastically) spreading apart the implant 100.

The notch 27 may alternatively to the semicircular shape comprise another form.

FIG. 8b shows the medial end face side of the implant 100.

FIG. 9a shows a capitulum implant 100 of a partial elbow joint replacement 1000 according to the present invention in a seventh exemplary embodiment. Compared to the third embodiment (FIG. 5), the inner contour (or inner surface shape 3) is continuously flat shaped, from the medial end section 7 to the lateral end section 5. This flat-shaped surface may prevent a rotation of the implant 100 after placing it on the capitulum 13. The implant 100 is secured against a rotation around the longitudinal axis x. Prior to implantation, the bone structure of the capitulum 13 may be processed and sawn laterally, for example, with the aid of a saw template. Subsequently, the implant 100 may be shifted laterally.

FIG. 9b shows a lateral view of the end face of the implant 100 and FIG. 9c shows a perspective view thereof.

FIG. 10a shows a capitulum implant 100 of a partial elbow joint replacement 1000 according to the present invention in an eighth exemplary embodiment. Compared to the embodiment of FIG. 9a, the inner contour 3 comprises additional surfaces and has a trapezoidal design in the cross section or in a section perpendicular to the longitudinal axis x. The inner contour 3 may comprise two, three or more surfaces.

FIG. 10b shows a medial view of the end face of the implant 100.

FIG. 11a shows a capitulum implant 100 of a partial elbow joint replacement 1000 according to the present invention having a conical shaft 29 as an anchoring device.

The anchoring mechanisms illustrated in FIGS. 11 to 16 may be combined with the illustrated and described embodiments of the inner contour (FIGS. 1, 4, 5, 6, 7, 8, 9, 10). The anchoring mechanisms may be optionally rounded respectively at corners and edges and/or the surfaces (of the respective anchoring mechanism) may be optimized through their surface roughness and/or through an optional coating for osteointegration.

All the anchoring mechanisms illustrated in FIGS. 11 to 16 may prevent a translational movement in the x direction and/or a rotational movement around the longitudinal axis of the implant 100.

The bone structures may be prepared for the anchoring mechanisms illustrated in FIGS. 11 to 16, for example by a reamer, a rasp and/or a saw or the like. The respective anchoring mechanism may be pressed into the capitulum or generally into the bone substance by a so-called press-fit. This may improve or accelerate the osteointegration of the implant 100.

In the anchoring mechanism, undercuts may be provided into which the bone structure can grow and thus increase a long-term stability of the implant 100.

The position of the respective anchoring mechanism is arranged and provided, in particular at the maximum radius of the capitulum and/or at the largest radius of the implant. The exact position and/or the angle at which the respective anchoring mechanism is inserted into the bone structure may vary on the patient depending on the intraoperative situation.

FIG. 11b shows a lateral view of the end face of the implant 100 having the conical shaft 29.

FIG. 12a, FIG. 12b and FIG. 12c show a capitulum implant 100 of a partial elbow joint replacement 1000 according to the present invention having a trapezoidal shaft 31 as an anchoring device.

FIG. 13a, FIG. 13b and FIG. 13c show a capitulum implant 100 of a partial elbow joint replacement 1000 according to the present invention having a wedge 33 as an anchoring device.

The wedge 33 extends in particular parallel to the axis of the rotation x of the implant 100 and of the elbow joint. The wedge 33 may have a so-called sawtooth profile, which can prevent a lateral displacement of the implant 100.

For inserting the implant 100 with the wedge 33 as an anchoring device into the bone, a notch may be sawn into the bone for bone preparation. The implant 100 may thereby be pushed from lateral side without spreading the bone apart of the elbow joint.

FIG. 14a, FIG. 14b and FIG. 14c show a capitulum implant 100 of a partial elbow joint replacement 1000 according to the present invention having a barb 35 as an anchoring device.

The barbs 35 are arranged on the inside of the implant 100. As shown in FIG. 14, the barbs 35 may be angular or alternatively conical. The radial expansion or height may be limited to 3 mm by way of example.

The implant 100 may advantageously be inserted into the bone without further pretreatment. A pre-drilling or the like is not necessary because of the small size of the barbs 35.

The barbs 35 may lead to or effect a primary stability of the implant 100 against translation (in longitudinal direction x) and/or against a rotation (around the longitudinal axis x).

The barbs 35 may alternatively or additionally arranged laterally at the edges in the circumferential direction 37 and/or only laterally or medially.

Figure 15A:
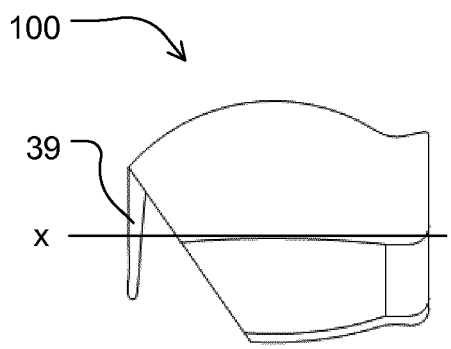
Figure 15B:
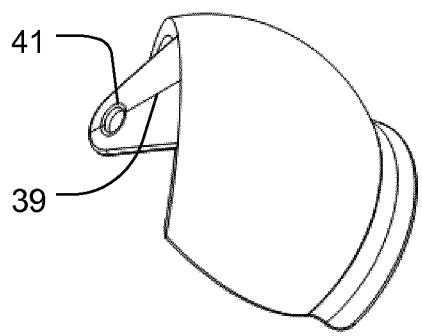
Figure 15C:
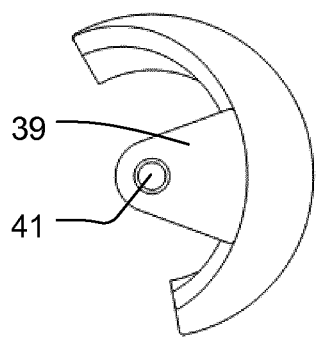

FIG. 15a, FIG. 15b and FIG. 15c show a capitulum implant 100 of a partial elbow joint replacement 1000 according to the present invention having a flap for fixing screws 39 as an anchoring device. The flap 39 may be referred to as a lug.

The flap 39 is laterally arranged at the end face of the implant 100. The flap comprises an opening 41 or bore which is arranged at the height of the rotation axis x. Through the opening 41, a screw may be introduced into the bone. This maintains and fixes the implant 100 in its position. The diameter of the screw may be purely exemplarily appr. 2 mm. When fixing or anchoring the implant 100 using the element 39 and a screw is introduced by the opening 41, there is particularly no further preparation, e.g. a predrilling of the bone, needed.

For implantation, the implant 100 can be guided, e.g. using the opening 41, through a guide wire, which is also used for processing (using milling and sawing) of the bone structure of the capitulum and/or of the elbow joint, and pushed onto the capitulum. The guide wire can subsequently be removed and the screw for fixing the implant can be inserted.

Figure 16A:
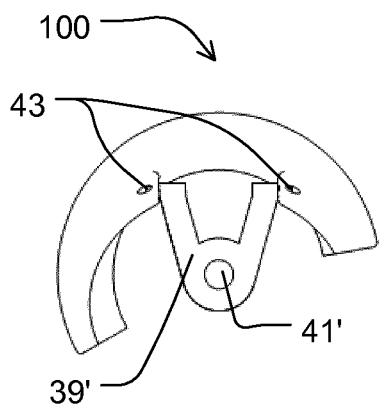
Figure 16B:
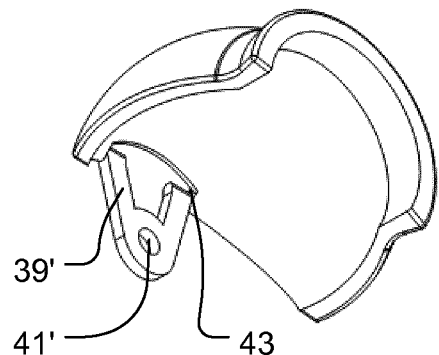

FIG. 16a and FIG. 16b show a capitulum implant 100 of a partial elbow joint replacement 1000 according to the present invention having a flap 39' for fixing screws as an anchoring device. The flap 39' is fixed by a hinge 43.

The flap 39' is attached to the implant 100 by the hinge 43. Due to the rotatability of the flap 39' relative to the implant 100 on the basis of the hinge 43 the implant 100 and the flap 39' may advantageously be adapted and optimized to the anatomical situation of the capitulum.

Optionally, the flap 39' may only be used for the guided application of the implant 100 to the implantation position on the capitulum, in order to decouple and remove the flap 39' after positioning the implant 100. For example, depending on the situation during implantation, another anchoring mechanism could be selected or, due to the inner contour, no further anchoring mechanism might be necessary.

FIG. 17a shows a radial head implant 200 of an elbow joint replacement 1000 according to the present invention.

The radial head implant 200 is provided for replacing the radial head (proximal, elbow-close). The aim of an implantation of a radial head implant 200 is to at least partially restore the articular mechanism, for example as a result of an arthrosis or after a traumatic event such as an accident. In particular, the sizes and proportions of the radial head implant 200 according to the present invention are based on an anatomical analysis.

The radial head implant 200 comprises a recess depth 45 which is adapted (varies with the implant sizes S/M/L/XL; see table according to FIG. 1e) to the radius (see table according to FIG. 1e, e.g. $R_4$) and to the height of the capitulum implant 100. The outer wall 47 of the radial head implant 200 is curved so that the radial head implant fits into the articular surface of the ulna (the lower arm bone encompasses the so-called spine or radius and the so-called ell or ulna, which together with the capitulum and the trochlea substantially form the elbow joint).

The radial head implant 200 may be made of one or more biocompatible materials, such as e.g. metal, ceramic, plastic, composite and/or a combination thereof. Examples of biocompatible materials are the metal alloy cobalt chromium molybdenum, the ceramics zirconium oxide, alumina oxide ($Al_2O_3$) or the plastics polyetheretherketone (PEEK), ultra-high molecular weight polyethylene (UHMWPE). Purely exemplarily, slide or glide pairings with the capitulum implant 100 and the radial head implant 200 could be a metal-plastic or ceramic-ceramic pairing. These slide pairings are known as low-abrasion material pairings and may therefore be advantageously used as a permanent pair of materials. Furthermore, such material pairings may be associated with a low risk of infection and/or with the avoidance of allergic reactions.

FIG. 17b shows a side view of the radial head implant 200.

FIG. 18 a-b show a radial head implant 200 having a wedge-shaped shaft 49 as an anchoring device.

The wedge-shaped shaft 49 may, like the below-described anchoring devices (see FIG. 19, 20, 21) be coated. A coating may improve or at least positively influence a so-called osteointegration (bone ingrowth or bone growth). A coating may, for example, comprise pure titanium, which is applied in a so-called plasma spray process with a layer thickness of approximately 40-50 μm and a roughness of approximately 7 μm. Alternatively, a coating may comprise hydroxyapatite, referred to as a so-called bone cement. Other coating materials and methods are also possible.

The wedge-shaped shaft 49 in FIGS. 18a and 18b comprise a rounded tip which may counteract additional or further damage to the bone during implantation. The lateral notches 51 of the wedge-shaped shaft 49 may favor or promote osteointegration. Furthermore, lateral notches 51 may increase the stability of the radial head implant 200, for example against a rotation around the longitudinal axis. The lateral notches 51 may be referred to as undercuts.

FIG. 19a, FIG. 19b and FIG. 19c show a radial head implant 200 according to the present invention having a wedge-shaped mandrel 53 as an anchoring device.

The wedge-shaped mandrels 53 may be referred to as flexible spikes which adapt to the respective surface when they are inserted into the bone (or medullary space). The mandrels 53 may be bent to the inside after being inserted in order to provide stability by tension in the mandrels 53 which are pressing against the bone. Optionally, the mandrels 53 may have barbs at the tip which "bury" themselves into the bone, thereby providing additional securing against slipping and/or rotation.

FIG. 20a and FIG. 20 b show a further radial head implant 200 according to the present invention having a short wedge 55 as an anchoring device.

The stability of the radial head implant 200 may be achieved predominantly by positioning and resting the head (upper part) of the radial head implant 200 on the cortical portion of the radial neck. The short wedge 55 may be inserted into the medullary space, or if there is still spongy bone present, into this region. Due to the little height of the wedge, a wide spreading of the joint line, of the bone or of the medullary space may be avoided. In this way, for example, soft tissue and/or ligaments may be protected and the natural joint stability may be maintained. The openings 57 may improve the ingrowth of the bone into the wedge 55 and thus allow a long-term stability of the implant 200.

FIG. 21a, FIG. 21b and FIG. 21c show a further radial head implant 200 according to the present invention having a T-shaped wedge 59 as an anchoring device.

The T-shape of the wedge 59 allow a generally high stability of the radial head implant 200 and generally permits a larger design spectrum of the radial head implant 200. The lateral side of the wedge 59 (in the upper region in FIGS. 21b and 21c) is rounded to the inside, whereby a wide spreading of the intra-articular space, of the bone or of the medullary space may be avoided.

The medial side of the wedge 59 (the lower region in FIGS. 21 and 21c) is wide and rounded so that the largest possible contact area with the bone can be created. The tip of the wedge 59 is rounded so that cutting into the bone may be avoided when the radial head implant 200 is inserted and the bone is not additionally damaged. The wedge 59 comprises a plateau toward the head so that the wedge can be supported on both sides by the bone. The wedge 59 can have a height of approximately 15 mm purely by way of example.

FIG. 22a, FIG. 22b and FIG. 22c show schematically the individual steps for introducing a radial head implant 200 into the medullary space 63 of the proximal radius 61. The position of the natural, already removed, radial head is shown in dashed lines.

The joint line 65 between the capitulum 13 and the proximal radius 61 may e.g. be already widened by removed bone material on the capitulum 13 or through atraumatic spreading apart, e.g. up to about 5 mm, so that the radial head implant 200 can be introduced, as shown in FIGS. 22a to 22c.

Figure 23:
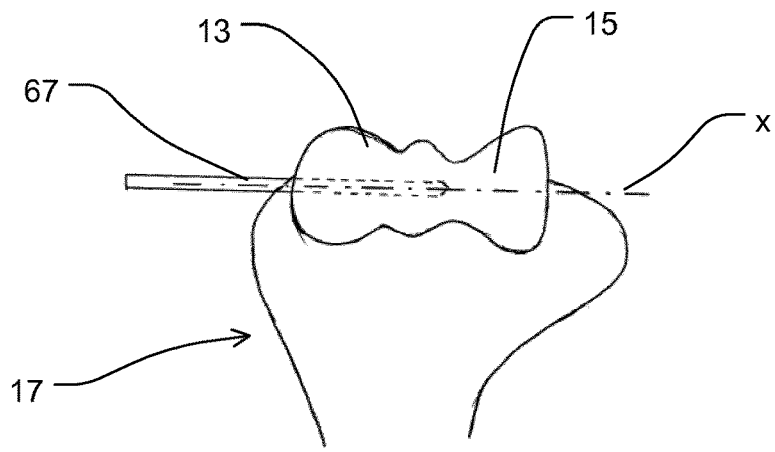
FIG. 23 shows the insertion of a K-wire into the distal humerus for preparing the implantation of a partial elbow joint replacement according to the present invention.

FIG. 23 shows the introduction of a K-wire 67 into the distal humerus 17 for preparing the implantation of a capitulum implant 100 according to the present invention. The K-wire 67, which comprises a diameter of approximately 2 mm, purely by way of example, is guided laterally (in FIG. 23 from the left) via the rotation axis x first into the capitulum and then into the trochlea. The rotation axis x is the natural rotation axis of the illustrated joint.

The K-wire 67 may be referred to as drill wire 67.

Figure 24:
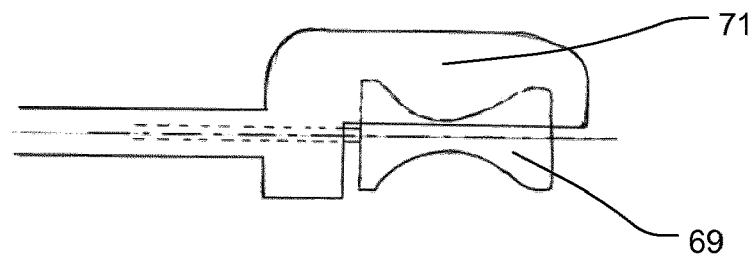
FIG. 24 shows a milling head with a tissue protector for machining or removing of bone structures.

FIG. 24 shows a milling head 69 having a tissue protector 71 for the machined removal of bone structures. The form of the milling head 69 (the milling head 69 may be referred to as a shaver) shows an almost anatomical shape in order to remove as little as possible of bone material from the surface. Alternatively the milling head 69 may comprise a simplified form of a barrel or container or a parabolic form. The tissue protector 71 remains unmoved during the milling process. The milling head 69 rotates about its own rotation axis and removes bone material in this way.

Figure 25:
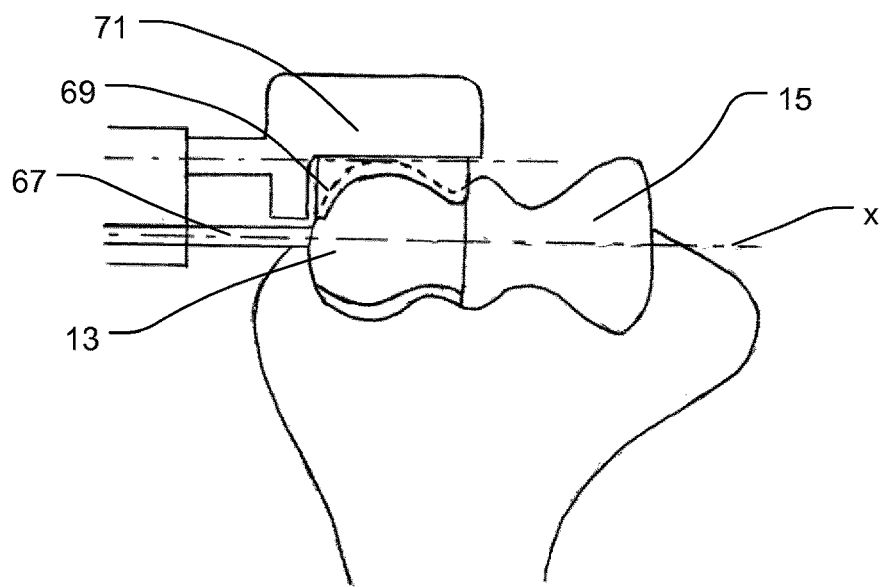
FIG. 25 shows the K-wire inserted into the milling head with a tissue protector while machining or removing of bone structures.
Figure 26A:
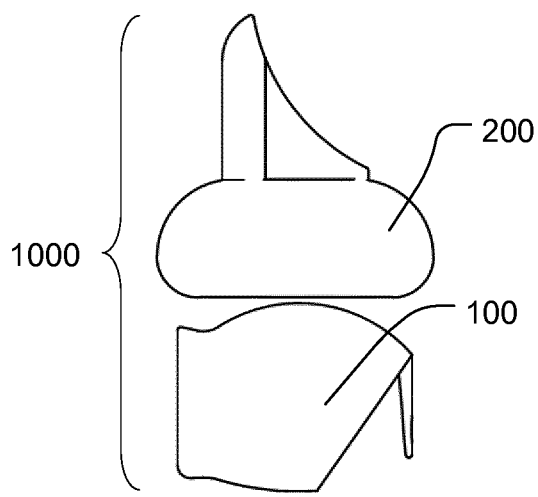
FIG. 26 a-f show different views of the partial elbow joint replacement according to the present invention with a capitulum implant as a shell-like segment and a radial head implant.
Figure 26B:
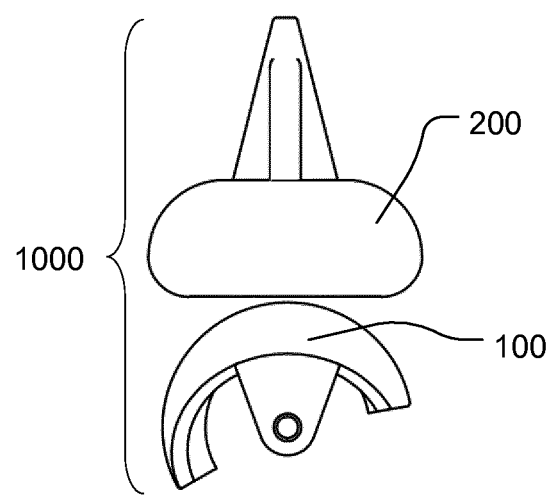
Figure 26C:
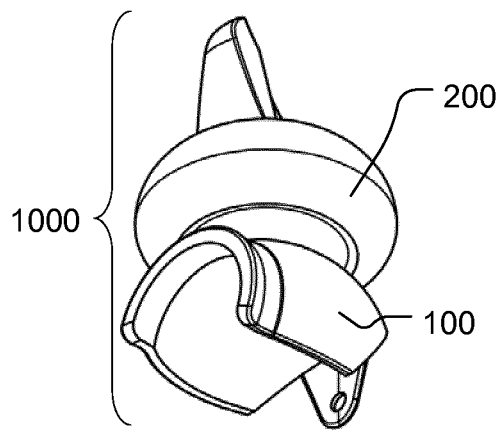
Figure 26D:
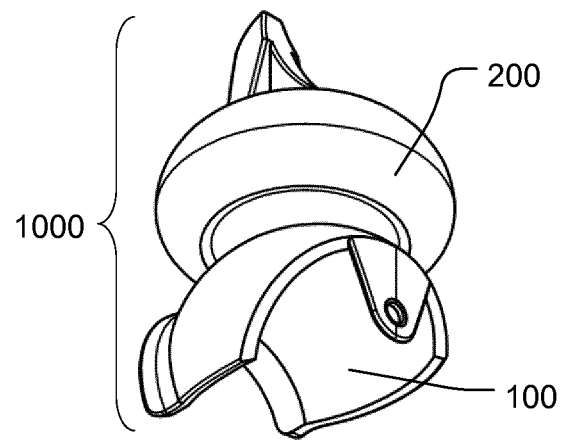
Figure 26E:
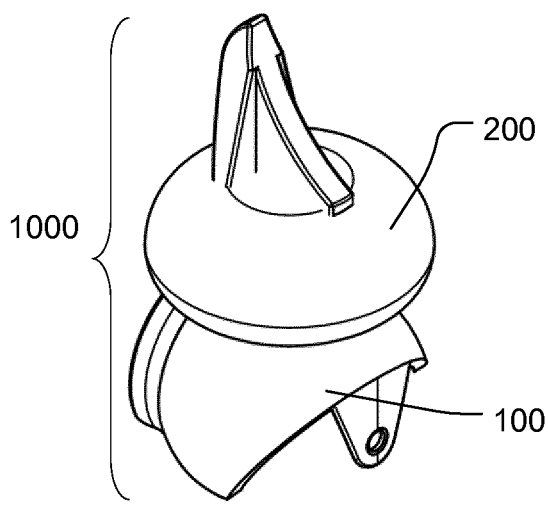
Figure 26F:
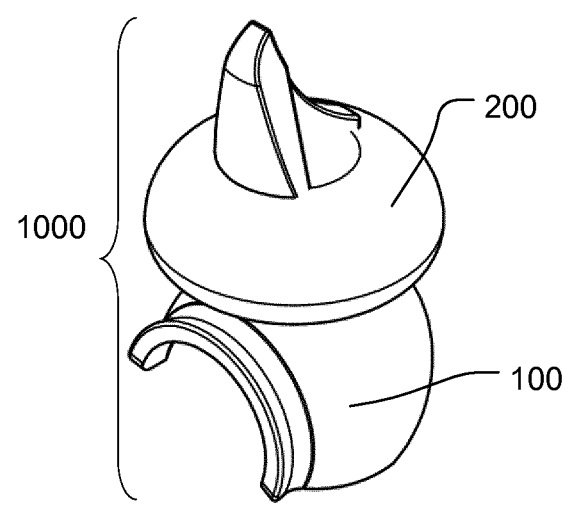

FIG. 25 shows the milling head 69 which was pushed on the K-wire 67 and the tissue protector 71 during removal of bone structures.

FIG. 26 a-f show different views of the partial elbow joint replacement 1000 according to the present invention having a capitulum implant as a shell-like segment 100 and a radial head implant 200.

LIST OF REFERENCE NUMERALS 1000 partial elbow joint replacement
100 capitulum implant; implant (part of a partial elbow joint replacement); shell-like segment
200 radius head implant (part of a partial elbow joint replacement)
x x-direction, longitudinal direction, longitudinal axis
r radial direction, direction perpendicular to the longitudinal direction
u circumferential direction
X1 length of the partial elbow joint replacement
X2 distance in x-direction of the implant from the medial end to the longitudinal position having the maximum radius of the implant
X3 distance in x-direction of the implant from the longitudinal position having the smallest radius between capitulum and trochlea and the longitudinal position with the maximum radius of the implant
R1 maximum radius of the implant perpendicular to the longitudinal direction
R2 smallest radius of the implant between capitulum and trochlea perpendicular to the longitudinal direction
R3 outer radius on the medial end face of the implant perpendicular to the longitudinal direction
R4 radius of the capitulum surface of the implant
R5 radius of the implant surface in the longitudinal direction between capitulum and trochlea
α angle to the radial direction
ß1, ß2 circumferential angle
1 outer surface shape, outer contour
3 inner surface shape, inner contour
5 lateral end; lateral end region; lateral end face; lateral section
7 medial end; medial end region; medial section
9 inflection point
11 elbow joint
13 capitulum
15 trochlea
17 humerus; distal humerus
19 longitudinal axis of the humerus; shaft axis of the humerus
21 cylindrical inner contour
23 cylindrical landing
25 notch in the circumferential direction u
27 notch in the longitudinal direction x
29 conical shaft (as anchoring device)
31 trapezoidal shaft (as anchoring device)
33 wedge (as anchoring device)
35 barb
37 edge (in circumferential direction)
39, 39' flap for fixing or fastening screws
41, 41' opening, bore
43 hinge
45 depth of recess
47 external wall of the radial head implant
49 wedge-shaped shaft
51 lateral notch
53 wedge-shaped mandrel
55 short wedge
57 opening (in the short wedge)
59 T-shaped wedge
61 proximal radius
63 medullary
65 joint line
67 K-wire; Kirschner wire
69 milling head
71 tissue protector

The invention claimed is:

1. A partial elbow joint replacement (1000) comprising:
a shell-like segment (100) along a longitudinal direction (x) with a concave inner contour (3) for its arrangement on or at at most a part of bone structures of an elbow joint of a patient, wherein the segment (100) comprises a lateral section (5) and a medial section (7); and
wherein an outer contour (1) of the segment (100) comprises at least one inflection point (9) in the longitudinal direction (x).

2. The partial elbow joint replacement (1000) according to claim 1, wherein the extension of the lateral section (5) in radial direction (r) is larger than the extension of the medial section (7) in radial direction (r).

3. The partial elbow joint replacement (1000) according to claim 1, wherein the shell-like segment (100) comprises no closed circumference in circumferential direction (u) which is perpendicular to the longitudinal direction (x) and/or perpendicular to the radial direction (r).

4. The partial elbow joint replacement (1000) according to claim 1, wherein the shell-like segment (100) comprises a wall thickness between 1 mm and 5 mm.

5. The partial elbow joint replacement (1000) according to claim 1, wherein the outer contour (1), at least in sections, has been adapted in a preoperative planning stage to be patient-specific by means of a computer imaging, in particular such that it conforms to the part of the bone structures of the elbow joint of the patient.

6. The partial elbow joint replacement (1000) according to claim 1, wherein the shell-like segment (100) comprises a rough inner contour surface (3).

7. The partial elbow joint replacement (1000) according to claim 1, wherein the inner contour (3) of the segment (100) is designed, in the longitudinal direction (x), in an analogous manner the outer contour (1) of the segment (100).

8. The partial elbow joint replacement (1000) according to claim 1, wherein the inner contour (3) of the segment (100) comprises in longitudinal direction (x) at least one inflection point (9).

9. The partial elbow joint replacement (1000) according to claim 1, wherein the inner contour (3) of the lateral section of the segment (100) comprises a concave, non-cylindrical contour, and wherein the inner contour (3) of the medial section of the segment (100) comprises a cylindrical contour in longitudinal direction (x).

10. The partial elbow joint replacement (1000) according to claim 1, wherein the inner contour (3) of the lateral section of the segment (100) comprises a concave, non-cylindrical contour, and wherein the inner contour (3) of the medial section of the segment (100) comprises a convex contour in longitudinal direction (x) which is radially bent to the inside.

11. The partial elbow joint replacement (1000) according to claim 1, wherein the inner contour (3) of the lateral section of the segment (100) comprises a concave, non-cylindrical contour, and wherein the inner contour (3) of the medial section of the segment (100) comprises a convex contour in the circumferential direction (u) which is radially bent to the inside.

12. The partial elbow joint replacement (1000) according to claim 1, wherein the inner contour (3) of the lateral section of the segment (100) comprises a cylindrical contour, and wherein the inner contour (3) of the medial section of the segment (100) comprises a convex contour in longitudinal direction (x) or a convex contour in circumferential direction (u).

13. The partial elbow joint replacement (1000) according to claim 1, wherein the shell-like segment (100) comprises at its lateral end section at the end face a fixing unit for fixing the shell-like segment (100) to the bone.

14. The partial elbow joint replacement (1000) according to claim 13, wherein the fixing unit encompasses a screw.

15. The partial elbow joint replacement (1000) according to claim 13, which is fixable in the bone parallel to the longitudinal direction (x) by the fixing unit.

16. The partial elbow joint replacement (1000) according to claim 1, wherein the segment (100) comprises at its inner side (3) at least one anchoring device for anchoring the segment (100) in a bone structure.

17. The partial elbow joint replacement (1000) according to claim 1, wherein the longitudinal direction (x) extends parallel to a rotation axis of the elbow joint, the longitudinal direction (x) is in the implanted state of the elbow joint replacement (1000) a rotation axis of the elbow joint and/or the longitudinal direction (x) is an epicondyle axis of the elbow joint.

18. The partial elbow joint replacement (1000) according to claim 1, wherein the inner side (3) of the segment (100) is shaped such that it conforms to a surface of a proximal ulna of the elbow joint.

19. The partial elbow joint replacement (1000) according to claim 1, wherein the segment (100) has at its lateral end an inlet or opening plane or wall which lies in a plane being under an angle (a) relative to the longitudinal direction (x).

20. The partial elbow joint replacement (1000) according to claim 19, wherein the angle (a) has a value within a range of 25° to 45°.

* * * * *